US00PP14332P29

(12) United States Plant Patent
Duncalf

(10) Patent No.: US PP14,332 P2
(45) Date of Patent: Dec. 2, 2003

(54) VARIETY OF AGAPANTHUS NAMED 'ATIBLU'

(50) Latin Name: *Agapanthus praecox orientalis*
Varietal Denomination: ATIblu

(75) Inventor: Ian Duncalf, Tauranga (NZ)

(73) Assignee: Anthony Tesselaar International Pty Ltd, Silvan (AU)

( * ) Notice: Subject to any disclaimer, the term of this patent is extended or adjusted under 35 U.S.C. 154(b) by 0 days.

(21) Appl. No.: 10/201,038

(22) Filed: Jul. 23, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Fulwider Patton Lee & Utecht, LLP

(57) ABSTRACT

A new and distinct cultivar of agapanthus plant named 'ATIblu' characterized as a floriferous plant having some 60–70 unique blue colored flowers on each clump within a few years and exhibiting a dwarf habit and good disease resistance.

1 Drawing Sheet

BACKGROUND OF THE NEW PLANT

The present invention comprises a new and distinct cultivar of agapanthus, botanically known as *Agapanthus praecox orientalis* and further known by the varietal name 'ATIblu'. The new variety was discovered in a selective breeding program by the inventor at Silvan, Victoria, Australia. The new variety is a sport selection from an *Agapanthus praecox orientalis* 'Snowstorm' (U.S. Plant Pat. No. 12,554). The new cultivar was selected from the progeny of this sport selection in a controlled environment by the inventor in Silvan, Victoria, Australia.

The new variety is the result of a selective breeding program taken from clump divisions at Silvan, Victoria, Australia in December of 1999. These divisions were selected and propagated through rhizome divisions selecting for differences in flower color and growth performance.

Continued observation of the vegetative divisions resulting from asexual reproduction of clump divisions taken at Silvan, Victoria, Australia have confirmed that the distinguishing features of this new cultivar came true, remain stable and are retained through successive propagation.

The new cultivar was grown in outdoors in trial beds at Silvan, Victoria, Australia. It is typically grown under natural light conditions in pots in a bark based potting media. Typical time from tissue division to flowering is eighteen (18) months.

The cultivar 'ATIblu' has not been observed under all environmental conditions. The phenotype may vary somewhat with variations in environment such as temperature and light intensity, without, however, any variance in genotype.

DESCRIPTION OF THE DRAWING

The accompanying drawing illustrates the new cultivar, the color being as nearly true as possible with color illustrations of this type. The photograph was taken in midsummer of a plant planted in July 2001 from tissue culture. The conditions on the day the photograph was taken were slightly overcast with no wind.

DESCRIPTION OF THE NEW PLANT

The following detailed description sets forth characteristics of the new cultivar. The data which defines each characteristic was collected from asexual reproductions grown outdoors, carried out by Anthony Tesselaar Plants at Silvan, Victoria, Australia. The plant histories were taken on liners, potted into 150 mm pots on approximately September 2001 and flowering in the first growing season on approximately November 2001. Color readings were taken indoors under natural filtered light using The Royal Horticultural Society of London Colour Chart.

THE PLANT

Classification:
- *Botanical.*—*Agapanthus praecox orientalis.*
- *Commercial.*—'ATIblu'.
- *Parentage.*—Sport of Agapanthus 'Snowstorm'.
- *Origin.*—Sport selection of *Agapanthus praecox* subspecies *orientalis* 'Snowstorm'.
- *Propagation.*—Clump division.
- *Rooting habit.*—Large, thick, and fleshy, about 5 mm thick.

Form:
- *Type.*—Dense, clump forming, perennial.
- *Height.*—Up to 700–850 mm.
- *Width.*—Clump up to 1000 mm.
- *Growth rate and habit.*—Upright growth habit; medium in size; growth rate is normal for this genus. Grows to full height in 18 months. Average for this species and genus.
- *Strength.*—Free standing.
- *Stem.*—Basal clump.

Leaves:
- *Arranged.*—Dense short leaves arranged in a clump with sessile base.
- *Shape.*—Narrow Acicular.
- *Length.*—Mean length of 360 mm.
- *Width.*—Mean width of 17 mm.
- *Margin.*—Entire and acute leaf apices.
- *Texture.*—Smooth.

*Color.*—Green Group RHS 137C to Yellow-Green Group RHS 137C.
*Venation.*—Parallel.

INFLORESCENCE

General appearance: Umbellate of blue flowers. Median length of flowering time is 90 days.
Borne:
Bud:
*Shape.*—Lanceolate, spathiate opening procedure of the entire umbel observed, sheath then falls away.
*Length.*—Up to 50 mm.
*Width.*—Up to 15 mm.
*Color.*—Green Group RHS145A with parallel green venations in the color of Green Group RHS143C.
Sepal:
*Quantity.*—None present.
Petals:
*Quantity.*—6 petals per floret.
*Size.*—Medium petal size approximately 8 mm wide by 35 mm long.
*Arrangement.*—Overlapping.
*Length.*—35–40 mm.
*Width.*—6–9 mm.
*Color.*—Midzone outside — Violet Blue Group RHS93C. Midzone inside — Violet Blue Group RHS93C. Margin inside — Violet Blue Group RHS92A. Basal spot — Violet Blue Group RHS92A.
Pedicel:
*Length.*—Mean length of 40–50 mm.
*Color.*—Green Group RHS138A.
Peduncle:
*Length.*—Mean length of 600–750 mm.
*Color.*—Yellow-Green Group RHS144A.
Flowers:
*Quantity.*—Very floriferous plant with some 60–70 flowers on each clump after only a few years and 30 florets per umbel.
*Time.*—Medium flowering time late spring/mid summer.
*Size.*—Approximately 160 mm.
*Profile upper.*—Umbellate.
*Profile lower.*—Umbel.
Fragrance: None detected.
Persistence:
*Disease resistence.*—Disease resistence is very good.
*Lasting quality.*—Lasts well as a cut flower, approximately 15 days depending on weather.

REPRODUCTIVE ORGANS

Stamens: Six stamens, attached to base of petals approximately 10 mm from base.
Filaments:
*Color.*—Violet Blue Group RHS92B.
Anther: Solitary marginal anther Purple Group RHS79A.
Pollen: Yellow Group 13C, present in small quantities.
Pistils:
*Style.*—Violet Group RHS88D.
*Ovary.*—Usually 3-sided Yellow-Green Group RHS151C, turns to Yellow-Green Group RHS144A once exposed to light.
Pollen:
*Color.*—Yellow Group RHS13C.
Seeds:
*Size.*—Mid sized, 20 mm long, 8 mm wide, 3 flat sides and separate compartments.
*Color.*—Yellow-Green Group RHS 144A.

GENERAL CHARACTERISTICS

'ATIblu' is primarily distinguished from plants of the Agapanthus cultivar 'Streamline' and other hybrid cultivars of Agapanthus genus by its uniquely colored blue flowers and from the parent plant 'Snowstorm' which has white flowers. 'ATIblu' is also more floriferous than other blue dwarf agapanthus selections and cultivars.

I claim:

1. A new and distinct variety of Agapanthus plant, substantially as shown and described.

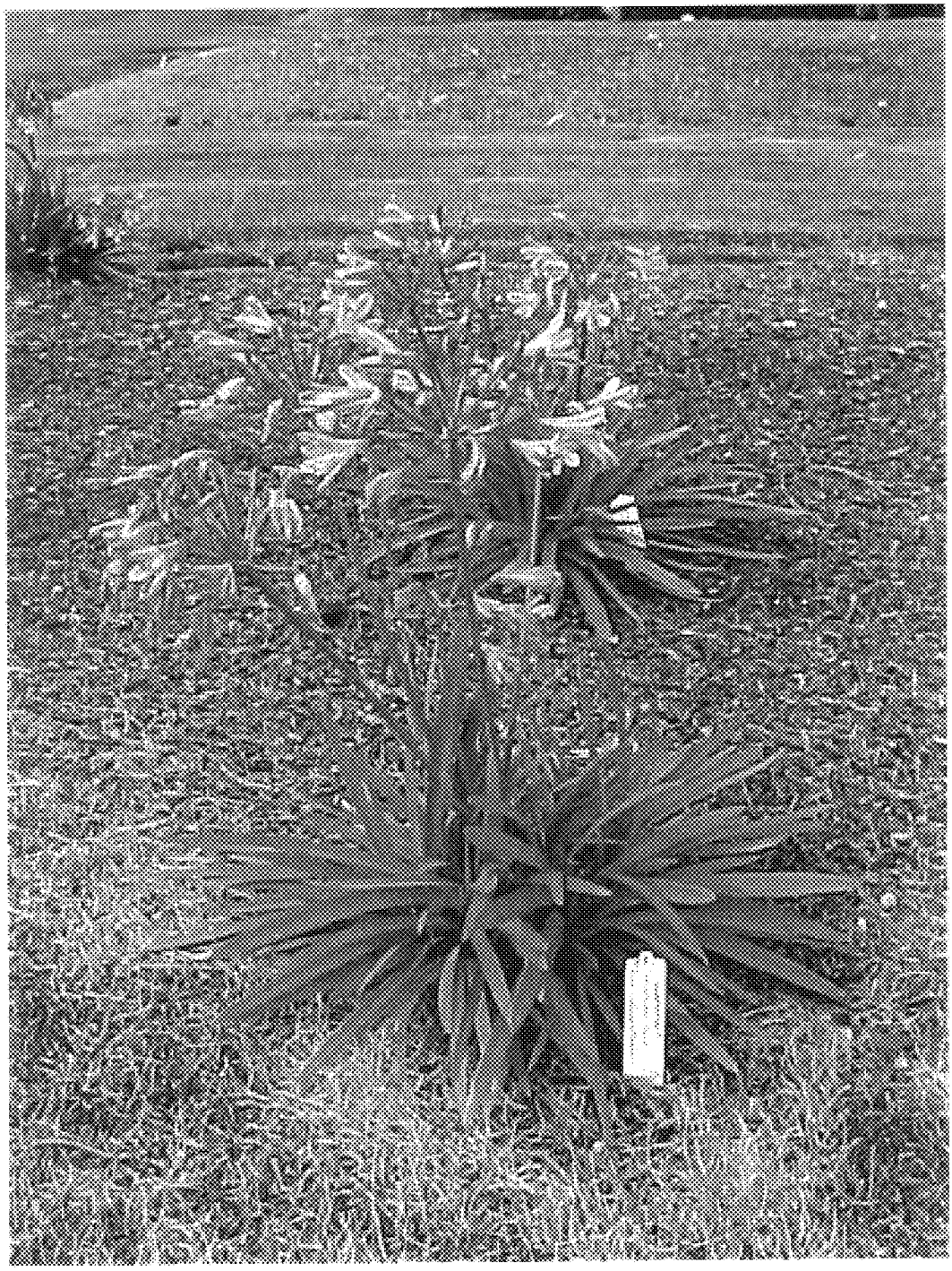

* * * * *